United States Patent
Shibata et al.

(10) Patent No.: US 11,312,804 B2
(45) Date of Patent: Apr. 26, 2022

(54) POLYMERIZABLE COMPOUND, POLYMERIZABLE COMPOSITION, POLYMER, AND PHOTORESIST COMPOSITION

(71) Applicant: JNC CORPORATION, Tokyo (JP)

(72) Inventors: Koichi Shibata, Kumamoto (JP); Teizi Satou, Kumamoto (JP); Daisuke Inoki, Kumamoto (JP); Hideki Hayashi, Kumamoto (JP)

(73) Assignee: JNC CORPORATION, Tokyo (JP)

( * ) Notice: Subject to any disclaimer, the term of this patent is extended or adjusted under 35 U.S.C. 154(b) by 0 days.

(21) Appl. No.: 16/968,874

(22) PCT Filed: Feb. 13, 2019

(86) PCT No.: PCT/JP2019/005076
§ 371 (c)(1),
(2) Date: Aug. 11, 2020

(87) PCT Pub. No.: WO2019/159957
PCT Pub. Date: Aug. 22, 2019

(65) Prior Publication Data
US 2021/0009546 A1 Jan. 14, 2021

(30) Foreign Application Priority Data
Feb. 16, 2018 (JP) .............................. JP2018-025633

(51) Int. Cl.
C07D 309/30 (2006.01)
C08F 220/28 (2006.01)
G03F 7/004 (2006.01)

(52) U.S. Cl.
CPC ........ C08F 220/283 (2020.02); C07D 309/30 (2013.01); C08F 220/281 (2020.02)

(58) Field of Classification Search
CPC ............... C07D 309/30; C08F 220/283; C08F 220/281; C08F 220/282; G03F 7/004; G03F 7/0045
USPC ...................................................... 549/292
See application file for complete search history.

(56) References Cited

U.S. PATENT DOCUMENTS

| | | | |
|---|---|---|---|
| 5,585,219 A | 12/1996 | Kaimoto et al. | |
| 6,280,898 B1 | 8/2001 | Hasegawa et al. | |
| 6,887,644 B1 | 5/2005 | Nozaki et al. | |
| 9,346,775 B2 * | 5/2016 | Ezoe .................... | C07D 307/33 |
| 2001/0026901 A1 | 10/2001 | Maeda et al. | |
| 2002/0009666 A1 | 1/2002 | Sato et al. | |
| 2004/0265732 A1 | 12/2004 | Maeda et al. | |
| 2005/0287473 A1 | 12/2005 | Kodama | |
| 2009/0061359 A1 | 3/2009 | Nozaki et al. | |
| 2011/0111345 A1 | 5/2011 | Allen et al. | |
| 2011/0223544 A1 | 9/2011 | Yada et al. | |
| 2013/0344442 A1 | 12/2013 | Sagehashi et al. | |
| 2014/0377706 A1 | 12/2014 | Hatakeyama et al. | |
| 2015/0212416 A1 | 7/2015 | Hatakeyama et al. | |
| 2016/0004157 A1 | 1/2016 | Ito et al. | |

FOREIGN PATENT DOCUMENTS

| | | |
|---|---|---|
| EP | 1980911 | 10/2008 |
| JP | H0439665 | 2/1992 |
| JP | H0580515 | 4/1993 |
| JP | H05257284 | 10/1993 |
| JP | H05265212 | 10/1993 |
| JP | H1112326 | 1/1999 |
| JP | 3042618 | 5/2000 |
| JP | 2001296661 | 10/2001 |
| JP | 2003040884 | 2/2003 |
| JP | 2004035602 | 2/2004 |
| JP | 2006146143 | 6/2006 |
| JP | 2008083370 | 4/2008 |
| JP | 4131062 | 8/2008 |
| JP | 2008281974 | 11/2008 |
| JP | 2009058632 | 3/2009 |
| JP | 2010047340 | 3/2012 |
| JP | 2014028926 | 2/2014 |
| JP | 2014178645 | 9/2014 |
| JP | 2015025029 | 2/2015 |
| JP | 2015026064 | 2/2015 |
| JP | 2015138236 | 7/2015 |
| KR | 2010080145 | * 7/2010 |

(Continued)

OTHER PUBLICATIONS

Koji Nozaki et al . A novel Polymer for A 193-nm Resist. (Year: 1996).*

(Continued)

*Primary Examiner* — John M Mauro
(74) *Attorney, Agent, or Firm* — JCIPRNET

(57) ABSTRACT

A polymerizable compound represented by formula (1). In formula (1), one of eight hydrogen atoms is substituted by a (meth)acryloyloxy group, and the rest seven hydrogen atoms are independently non-substituted or substituted by a saturated hydrocarbon group having 1 to 10 carbons.

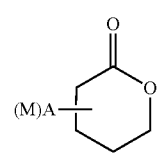

(1)

6 Claims, No Drawings

(56) References Cited

FOREIGN PATENT DOCUMENTS

KR    20100080145    7/2010

OTHER PUBLICATIONS

"International Search Report (Form PCT/ISA/210) of PCT/JP2019/005076," dated May 21, 2019, with English translation thereof, pp. 1-4.
Registry(SIN) [Online], "CAS registration No. 617711-92-9," retrieved on May 8, 2019.

* cited by examiner

POLYMERIZABLE COMPOUND, POLYMERIZABLE COMPOSITION, POLYMER, AND PHOTORESIST COMPOSITION

CROSS-REFERENCE TO RELATED APPLICATION

This application is a 371 application of the international PCT application serial no. PCT/JP2019/005076, filed on Feb. 13, 2019, which claims the priority benefit of Japan application no. 2018-025633, filed on Feb. 16, 2018. The entirety of each of the abovementioned patent applications is hereby incorporated by reference herein and made a part of this specification.

TECHNICAL FIELD

The invention relates to polymerizable compounds, polymerizable compositions containing the polymerizable compounds, polymers formed by polymerizing the polymerizable compositions, and photoresist compositions containing the polymers.

BACKGROUND ART

With achievement of high integration and high speed of LSI, a pattern rule is rapidly getting finer and finer. As a cutting-edge fine patterning technology, a 45-32 nm node device by ArF immersion lithography is implemented on the commercial stage. As a next-generation of 32 nm or smaller node, studies on such as immersion lithography using an ultra-high NA lens formed by combining a liquid having a refractive index higher than water, a high refractive index lens and a high refractive index resist film, a extreme ultraviolet (EUV) lithography (13.5 nm), multiple exposure of ArF lithography (multiple patterning lithography) and the like have been conducted, and some of the devices have already been put in practical use.

In recent years, in addition to the above-described patterning methods, a negative tone resist using organic solvent development has also attracted attention. As a significantly fine hole pattern that cannot be achieved by a positive tone is developed by the exposure of a negative tone, a high resolution negative pattern is formed using a positive photoresist composition, which can achieve high resolution, with organic solvent development.

As an ArF photoresist composition for negative tone development with an organic solvent, a patterning method in which a positive ArF photoresist composition of conventional type can be used is disclosed (Patent literature No. 1).

Requirements in common with a photoresist material used in the developing method include substrate adhesion, sensitivity, resolution, dry etching resistance, less unevenness of both the coated film and the dried film and drying unevenness, no pattern collapse and no crack into the film. Then, in order to satisfy the required characteristics, as a resin component, it is essential to have a unit with a high-polar pendant and a unit with a bulky pendant. The high-polarity unit is mainly effective in enhancing the resin adhesion onto the substrate, and methacrylates having a monocyclic lactone, such as a butyrolactone ring and a valerolactone ring, or the like have been developed so far (Patent literature Nos. 2 to 5). The bulky unit is mainly effective in enhancing the dry etching resistance, and methacrylates having a skeleton of adamantane, norbornane or the like have been developed so far (Patent literature Nos. 6 to 9). Further, methacrylates having a fused ring lactone as typified by methacrylate of norbornane lactones in which both functions are simultaneously provided for one pendant has been proposed (Patent literature Nos. 10 to 12).

In order to meet a further fine-patterning requirement, monomers for a base resin for a photoresist having excellent required characteristics have been energetically developed.

CITATION LIST

Patent Literature

Patent literature No. 1: JP 2008-281974 A.
Patent literature No. 2: JP 4012600 B.
Patent literature No. 3: JP 4139948 B.
Patent literature No. 4: JP 6221939 B.
Patent literature No. 5: JP 6044557 B.
Patent literature No. 6: JP 2881969 B.
Patent literature No. 7: JP 3000745 B.
Patent literature No. 8: JP 3221909 B.
Patent literature No. 9: JP H05-265212 A.
Patent literature No. 10: JP 3042618 B.
Patent literature No. 11: JP 4131062 B.
Patent literature No. 12: JP 2006-146143 A.
Patent literature No. 13: JP 5045314 B.
Patent literature No. 14: JP 6126878 B.
Patent literature No. 15: JP 5494489 B.
Patent literature No. 16: JP 2003-40884 A.

SUMMARY OF INVENTION

Technical Problem

When a (meth)acrylate having a δ-lactone skeleton is incorporated into a resin by a polymerization reaction, it plays a role of enhancing resin adhesion onto the substrate. The compound is obtained by first synthesizing hydroxylactone as a precursor thereof, and (meth)acryloylating the hydroxy group on the hydroxylactone. Above all, mevalonolactone methacrylate has a simple structure, and therefore is commercially available. A polymer having a unit derived therefrom is also known to exhibit excellent characteristics as a photoresist resin (Patent literature Nos. 13 to 15).

However, mevalonolactone methacrylate is significantly expensive, which stands as an obstacle to market expansion of the compound, a polymer having the compound as a monomer unit, and a photoresist resin composition containing the polymer.

The reason why mevalonolactone methacrylate is expensive is that expensiveness of mevalonolactone as a precursor thereof, expensiveness of 3-methylpentane-1,3,5-triol as a raw material thereof, and also high hydrophilicity of both mevalonolactone methacrylate and mevalonolactone make the mass production of mevalonolactone methacrylate difficult. High hydrophilicity requires extraction from an aqueous layer with an organic solvent more frequently than ordinary, and an extraction solvent essentially needs to be polar such as ethyl acetate. Patent literature No. 16 discloses a production method of mevalonolactone, in which extraction with ethyl acetate is performed as many as 6 times. Further, such a polar solvent has relatively high miscibility with water, and therefore many times of extraction operation causes incorporation of a significant amount of water into the organic layer. In the case that the reaction is carried out at a laboratory scale, the number of times of extraction can be easily increased and the organic layer after extraction can be easily dried over a desiccant such as anhydrous magnesium sulfate. However, in the case of production on a plant scale, such operation is difficult.

For such reasons, development of a polymerizable compound that can be derived from hydroxylactone having low hydrophilicity, and that can be used as a raw material of a photoresist composition in place of mevalonolactone methacrylate, has been desired. Accordingly, the invention provides a new polymerizable compound that can be used as a raw material of a photoresist composition, or the like.

Solution to Problem

As a result of the inventors having diligently continued to conduct study, it was found that (meth)acrylate having a specific structure is a polymerizable compound that solves the above-described problems, and is suitable for production of a photoresist polymer, and thus have reached the invention. The invention includes a structure as described below.

The relative configuration and the diastereomer ratio can be ignored when the compounds described in the formulas below have diastereomers based on the configurations of the substituents on the lactone ring.

Item 1. A polymerizable compound, represented by formula (1):

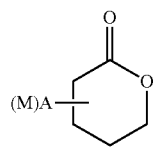

(1)

wherein, in formula (1), (M)A is a (meth)acryloyloxy group, and one of eight hydrogen atoms on the lactone ring is substituted by the (meth)acryloyloxy group, and the rest of the seven hydrogen atoms are independently non-substituted or substituted by a saturated hydrocarbon group having 1 to 10 carbons.

Item 2. A polymerizable compound, represented by formula (1-1):

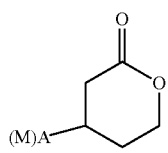

(1-1)

wherein, in formula (1-1), (M)A is (meth)acryloyloxy group, and seven hydrogen atoms on the lactone ring are independently non-substituted or substituted by a saturated hydrocarbon group having 1 to 10 carbons.

Item 3. The polymerizable compound according to item 2, wherein, in formula (1-1), (M)A is (meth)acryloyloxy group, and seven hydrogen atoms on the lactone ring are independently non-substituted or substituted by a saturated hydrocarbon group having 1 to 4 carbons.

Item 4. A polymerizable compound, represented by formula (1-2):

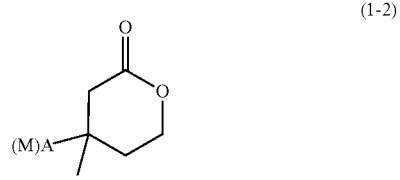

(1-2)

wherein, in formula (1-2), (M)A is (meth)acryloyloxy group, and six hydrogen atoms on the lactone ring are independently non-substituted or substituted by a saturated hydrocarbon group having 1 to 4 carbons.

Item 5. A polymerizable compound, represented by formula (1-3):

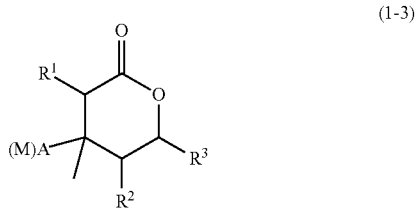

(1-3)

wherein, in formula (1-3), (M)A is (meth)acryloyloxy group, and one of $R^1$, $R^2$ and $R^3$ is a saturated hydrocarbon group having 1 to 4 carbons, and the rest of the two are hydrogen atoms.

Item 6. A polymerizable compound, represented by formula (1-4):

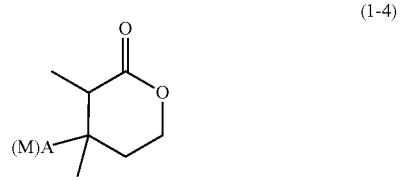

(1-4)

wherein, in formula (1-4), (M)A is (meth)acryloyloxy group.

Item 7. A polymerizable compound, represented by formula (1-5):

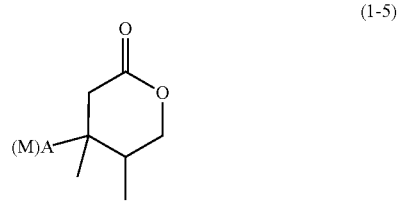

(1-5)

wherein, in formula (1-5), (M)A is (meth)acryloyloxy group.

Item 8. A polymerizable compound, represented by formula (1-6):

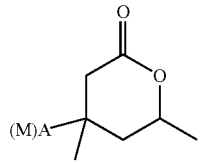

(1-6)

wherein, in formula (1-6), (M)A is (meth)acryloyloxy group.

Item 9. A polymerizable composition, containing at least one polymerizable compound according to any one of items 1 to 8.

Item 10. A polymer, formed by polymerizing the polymerizable composition according to item 9.

Item 11. A photoresist composition, containing the polymerizable composition according to item 9 and a photoacid generator.

Item 12. A photoresist composition, containing the polymer according to item 10 and a photoacid generator.

Advantageous Effects of Invention

A polymerizable compound (δ-lactone-based (meth)acrylate) developed in the invention can be produced more easily than mevalonolactone methacrylate that is an existing compound. Further, a photoresist composition containing a resin having the units derived from the polymerizable compounds can exhibit photoresist characteristics equivalent to or superior to those from mevalonolactone methacrylate. Thus, as a result, the photoresist composition can be easily and inexpensively provided without degrading the photoresist characteristics.

DESCRIPTION OF EMBODIMENTS

Hereinafter, embodiments for carrying out the invention will be described in details, and it should be understood that the invention is not limited to the following embodiments, and modifications and improvements appropriately made on the following embodiments based on ordinary knowledge of those skilled in the art without departing from the spirit of the invention also fall within the scope of the invention.

In formula (1), one of eight hydrogen atoms on the lactone ring is substituted by (meth)acryloyloxy group, and the rest of the seven hydrogen atoms are independently non-substituted or substituted by the saturated hydrocarbon groups having 1 to 10 carbons.

Examples of the saturated hydrocarbon groups having 1 to 10 carbons in formula (1) include —$CH_3$, —$C_2H_5$, —$CH_2CH_2CH_3$, —CH($CH_3$)$_2$, —$CH_2CH_2CH_2CH_3$, —$CH_2CH(CH_3)_2$, —C($CH_3$)$_3$, —CH($CH_3$)$CH_2CH_3$, —$CH_2(CH_2)_3CH_3$, —$CH_2CH(CH_3)CH_2CH_3$, —$CH_2CH_2CH(CH_3)_2$, —CH($CH_3$)$CH_2CH_2CH_3$, —CH($CH_2CH_3$)$_2$, —$CH_2C(CH_3)_3$, —CH($CH_3$)CH($CH_3$)$_2$, —C($CH_3$)$_2CH_2CH_3$, cyclopentyl, —$CH_2(CH_2)_4CH_3$, —$CH_2(CH_2)_2CH(CH_3)_2$, —$CH_2CH_2CH(CH_3)CH_2CH_3$, —$CH_2CH(CH_3)(CH_2)_2CH_3$, —CH($CH_3$)($CH_2$)$_3CH_3$, —$CH_2CH(CH_3)CH(CH_3)_2$, —CH($CH_3$)$CH_2CH(CH_3)_2$, —C($CH_3$)$_2CH(CH_3)_2$, —CH($CH_3$)C($CH_3$)$_3$, —CH($CH_2CH_3$)CH($CH_3$)$_2$, —CH($CH_2CH_3$)($CH_2$)$_2CH_3$, cyclohexyl, 2-methylcyclopentyl, 3-methylcyclopentyl, cyclopentylmethyl, —$CH_2(CH_2)_5CH_3$, 2-methylcyclohexyl, 3-methylcyclohexyl, 4-methylcyclohexyl, cyclohexylmethyl, —$CH_2(CH_2)_6CH_3$, —$CH_2(CH_2)_7CH_3$ and —$CH_2(CH_2)_8CH_3$.

Among the groups, —$CH_3$ and —$C_2H_5$ are preferred.

In formula (1), one to four hydrogens of seven hydrogens that are not substituted by (meth)acryloyloxy group are preferably substituted by a saturated hydrocarbon group having 1 to 10 carbons, and two to three hydrogens thereof are further preferably substituted by a saturated hydrocarbon group having 1 to 10 carbons.

Moreover, when any hydrogen in formula (1) is substituted by a saturated hydrocarbon group having 1 to 10 carbons, at least one of the substituted sites thereof is preferably the β-position from the carbonyl group.

In formula (1), a lactone moiety is a protective group of (meth)acrylic acid, and has a function of being deprotected by acid. The reaction mechanism thereof is E1 elimination, and therefore the bonding position of (meth)acryloyloxy group on the lactone ring is preferably at the β-position from the carbonyl group of the lactone. Accordingly, the polymerizable compound represented by formula (1) preferably has a structure represented by formula (1-1).

In formula (1-1), one to four hydrogens of seven hydrogens that are not substituted by (meth)acryloyloxy group are preferably substituted by a saturated hydrocarbon group having 1 to 10 carbons, and two to three hydrogens thereof are further preferably substituted by a saturated hydrocarbon group having 1 to 10 carbons. Moreover, Examples of the saturated hydrocarbon group having 1 to 10 carbons include the same groups as in the Examples in formula (1), and preferred examples also include the same groups as in the examples in formula (1).

The lactone moiety included in the unit of the polymer obtained by polymerizing the polymerizable compound represented by formula (1-1) has a role of enhancing adhesion between the polymer and a substrate by high polarity thereof. Accordingly, in formula (1-1), introduction of an alkyl group of many carbons onto the lactone ring reduces its hydrophilicity. Thus, although such introduction is advantageous in the extraction step upon production, it is disadvantageous in terms of substrate adhesion because of its lower polarity.

Accordingly, the number of carbons of the alkyl group on the lactone ring is preferably 4 or less, which is not so many, and methyl (—$CH_3$) or ethyl (—$C_2H_5$) is further preferred.

Further, in order to efficiently proceed the E1 elimination that is a deprotection reaction, in formula (1) or (1-1), a structure in which carbocation is easily generated on the carbon atom having the (meth)acryloyloxy group is preferred, and as such a structure, the carbon atom is preferably a tertiary carbon to a secondary carbon. Accordingly, the polymerizable compound represented by formula (1-1) preferably has a structure represented by formula (1-2).

In formula (1-2), six hydrogen atoms on the lactone ring are independently non-substituted or substituted by a saturated hydrocarbon group having 1 to 4 carbons. Examples of the saturated hydrocarbon group having 1 to 4 carbons include —$CH_3$, —$C_2H_5$, —$CH_2CH_2CH_3$, —CH($CH_3$)$_2$, —$CH_2CH_2CH_2CH_3$, —$CH_2CH(CH_3)_2$ and —C($CH_3$)$_3$. Among the groups, methyl (—$CH_3$) or ethyl (—$C_2H_5$) is preferred.

The number of the saturated hydrocarbon groups having 1 to 4 carbons in the polymerizable compound represented by formula (1-2) is preferably one because it can suppress the hydrophilicity while maintaining the substrate adhesion of the resin, and accordingly a structure represented by formula (1-3) is preferred.

Examples of the saturated hydrocarbon group having 1 to 4 carbons in the compound represented by formula (1-3) include the same groups as in the examples in formula (1-2), and methyl is further preferred for maintaining a good balance between better substrate adhesion and lower hydrophilicity. Accordingly, the group preferably has a structure represented by formula (1-4), formula (1-5) or formula (1-6).

In the polymerizable compound represented by formula (1), there may be diastereomers derived from the relative configuration of the substituents on the lactone ring. In general, in a reaction in which the diastereomers can be formed, formation of a single compound with selectivity of 100% is significantly rare. Accordingly, with regard to the polymerizable compound represented by formula (1), a diastereomer mixture is highly likely to be obtained during a production process except for a compound in which the diastereomer cannot structurally exist. In such a case, the diastereomers may be separated, but do not need to be separated if the diastereomer mixture can be used as a photoresist composition without any problem. Moreover, physical properties can be adjusted by mixing the diastereomers at an arbitrary ratio after separation. The diastereomer separation can be carried out either when the mixture is formed or when they are easily separable in the later process.

The polymerizable compound represented by formula (1) can be produced according to various methods by making full use of a technique of synthetic organic chemistry. Examples thereof are described below, but the scope of the invention is not limited by the examples.

As shown in reaction scheme [I] below, a route using an addition reaction of ketene to the compound represented by formula (8) (Tetrahedron, 1959, Vol. 5, pp. 311-339), or as shown in reaction scheme [II], a route through an intramolecular Reformatsky reaction using a compound represented by formula (11) as a starting material (JP 2000-80090 A), or the like can be applied.

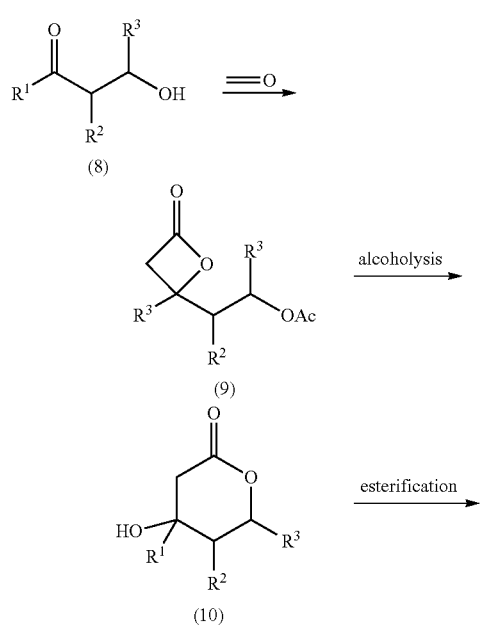

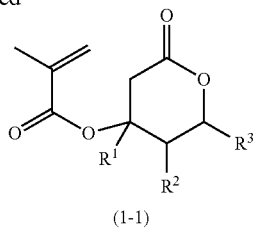

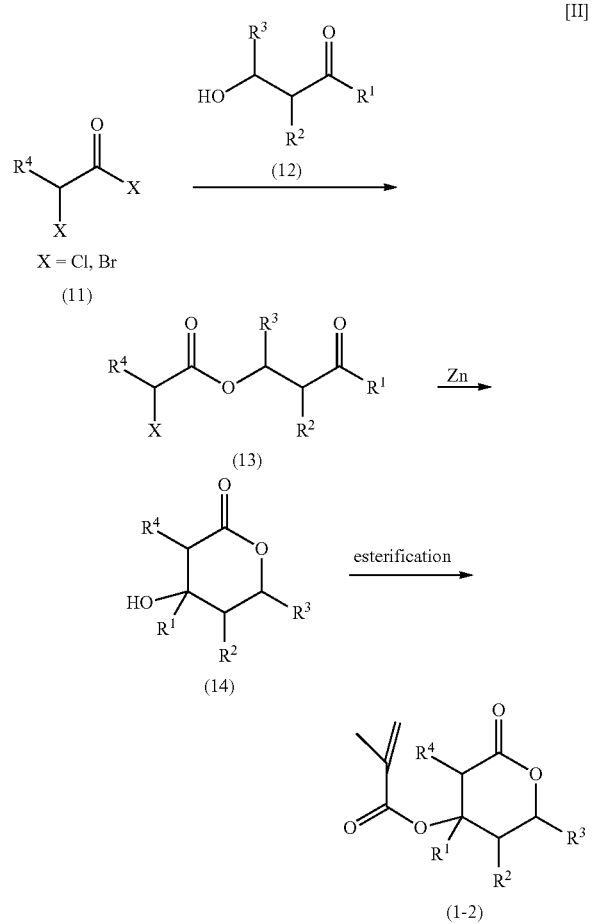

An embodiment of the invention also relates to a polymerizable composition containing at least one polymerizable compound represented by formula (1). The polymerizable composition according to the embodiment of the invention ordinarily contains 1 to 90% by weight, and preferably 10 to 70% by weight of the polymerizable compound represented by formula (1) based on the total amount of the polymerizable composition.

Into the polymerizable composition according to the embodiment of the invention, for example, a surfactant can be added, in addition to the polymerizable compound represented by formula (1).

A photoresist composition according to the embodiment of the invention contains, as a basic component, a polymer used as a base resin, or a polymerizable composition containing a polymerizable compound from which the polymer is formed, and a compound that can generate acid when the compound is decomposed by absorbing an appropriate amount of imaging radiation, and can eliminate an alcohol moiety of an ester group of the polymer (photoacid generator: hereinafter, also described as PAG). The photoresist composition according to the embodiment of the invention may be further formed of a solvent, and other components added thereto, when necessary.

A content of the polymer obtained by polymerizing the polymerizable compound represented by formula (1), to be contained in the photoresist composition according to the embodiment of the invention, is ordinarily 1 to 90% by weight, and preferably 10 to 70% by weight based on the total amount of the photoresist composition.

Meanwhile, a content of the polymerizable composition containing the polymerizable compound represented by formula (1), to be contained in the photoresist composition according to the embodiment of the invention, is ordinarily 1 to 99% by weight, and preferably 10 to 95% by weight.

The polymer used as the base resin includes, as a first unit, a $\delta$-lactone structure derived from the polymerizable compound represented by formula (1). Moreover, the polymer used as the base resin preferably includes, as a second unit, a structure having an acid-sensitive protective group in a side chain of the polymer, and may include, as a third unit, any other unit, or the polymer may be various polymers such as a terpolymer.

Further, in addition to the first unit including the above-described lactone moiety as the protective group, the second unit of the polymer used as the base resin preferably has a protected carboxyl group. More specifically, an acid-sensitive polymer (copolymer) as the base resin may include, as the second unit, the one including the carboxyl group unstable to acid, and such a combination is also preferred.

Examples of the polymerizable compound leading to such a unit include methacrylate of tertiary alcohol.

The third unit of the polymer used as the base resin is preferably the one derived from a (meth)acrylate-based polymerizable compound having a protected carboxyl group, the one derived from a vinyl phenol-based polymerizable compound, the one derived from an N-substituted maleimide-based polymerizable compound, the one derived from a styrene-based polymerizable compound, or the one having an ester group containing a monocyclic alicyclic hydrocarbon moiety. Moreover, as having an unit including a structure typified by adamantyl group, norbornyl group or the like in a polycyclic alicyclic hydrocarbon part improves dry etching resistance, such a case is further preferred.

In the polymer according to the embodiment of the invention, the (molar) ratio of the first, the second, and the third units are, for example, 0.1 to 0.8, 0.1 to 0.5, and 0.1 to 0.5, respectively. The polymer including neither the second unit nor the third unit can be exemplified.

A type of a polymerization reaction upon producing the polymer according to the embodiment of the invention is not particularly limited, and examples thereof include radical polymerization, ionic polymerization, polycondensation and coordination polymerization. Moreover, a type of polymerization is not limited, either, and solution polymerization, bulk polymerization, emulsion polymerization or the like can be used, for example.

In the photoresist composition according to the embodiment of the invention, when a PAG is exposed to imaging ray after formation of a photoresist film, PAG absorbs the ray to generate acid. Subsequently, when the photoresist film after the exposure is heated, the acid previously generated catalytically acts thereon, and the deprotection reaction proceeds in the exposed area of the film.

PAG can be selected from photoacid generators generally used in photoresist chemistry, namely, from among substances that generate protonic acid on irradiation with the rays such as ultraviolet ray, far ultraviolet ray, vacuum ultraviolet ray, an electron beam, X-rays and a laser beam. Use thereof is not particularly limited, and the substance can be appropriately selected from among publicly-known substances according to the purpose. Examples thereof include: onium salts such as diphenyliodonium salt and triphenylsulfonium salt; sulfonates such as benzyl tosylate and benzyl sulfonate; and a halogenated organic compounds such as dibromobisphenol A and trisdibromopropyl isocyanurate. These substances may be used alone or in combination of two or more.

Content of the photoacid generator in the photoresist composition can be appropriately selected according to the strength of acid generated by exposure, a ratio of each unit in the polymer or the like, and can be selected from ranges of 0.1 to 30 parts by weight, preferably 1 to 25 parts by weight, and further preferably about 2 to about 20 parts by weight based on polymer being taken as 100 parts by weight, for example.

In the photoresist composition according to the embodiment of the invention, the solvent is not particularly limited, and a general-purpose photoresist solvent can be used. Examples thereof preferably include propylene glycol methyl ether acetate, ethyl lactate, 2-heptanone and cyclohexanone. Moreover, as an auxiliary solvent, propylene glycol monomethyl ether, $\gamma$-butyrolactone or the like may be further added thereto. Especially in the case of immersion exposure, among the solvents, from the viewpoint of rapid coating of the photoresist composition and achieving good coating properties, organic solvents having a boiling point of about 100 to about 200° C. and good resin-dissolving ability are preferred.

Other components are not particularly limited as long as the components do not affect the effects of the invention, and can be appropriately selected according to the purpose. Examples thereof include commonly-known various additives. For example, when the purpose is to improve exposure contrast, a quencher can be added thereto, and when the purpose is to improve the coating properties, a surfactant can be added thereto.

The quencher is not particularly limited, and can be appropriately selected. Examples thereof preferably include a nitrogen-containing compound typified by tri-n-octylamine, 2-methylimidazole, 1,8-diazabicyclo[5.4.0]undec-7-ene (DBU) and 1,5-diazabicyclo[4.3.0]non-5-ene (DBN).

The surfactant is not particularly limited, and can be appropriately selected. A nonionic surfactant containing no metal ion such as sodium salt, potassium salt or the like is preferred. Examples of such a surfactant preferably include a surfactant selected from a polyoxyethylene-polyoxypropylene condensate-based surfactant, a polyoxyalkylene alkyl ether-based surfactant, a polyoxyethylene alkyl ether-based surfactant, a polyoxyethylene derivative-based surfactant, a sorbitan fatty acid ester-based surfactant, a glycerol fatty acid ester-based surfactant, a primary alcohol ethoxylate-based surfactant, a phenol ethoxylate-based surfactant, a silicone-based surfactant and a fluorine-based surfactant. The surfactants may be used alone, or in combination of two or more. Moreover, even an ionic surfactant can be used if the surfactant is a nonmetallic salt-based surfactant, and an improvement effect of the coating properties can be similarly obtained.

When a film of the photoresist composition according to the embodiment of the invention is formed on a quartz substrate, absorbance in a wavelength of 180 to 300 nm of an exposed ray is preferably 1.75 or less. At absorbance over 1.75, when a photoresist film thickness is adjusted to 0.4 micrometer, transmittance becomes 20% or less, and thus the patterning significantly becomes dissatisfactory.

EXAMPLES

Synthesis Example

Synthesis of polymerizable compounds suitable for the polymer contained in the photoresist composition according to the embodiment of the invention are as follows, but the invention is not limited to the examples. Moreover, with regard to structures shown below, it should be considered that the compounds whose configurations are shown in figures are actually enantiomeric mixtures in an equal amount, namely, a racemate.

A reaction was monitored by thin layer chromatography (TLC) or gas chromatography (GC), and the structure of a compound obtained was determined by a nuclear magnetic resonance (NMR) spectrum, and purity thereof was measured by GC. First, an analysis apparatus and an analysis method will be described.

TLC

Merck KGaA Silica gel 60 F254 TLC plates were cut out into a rectangle of 1.5 cm×5.0 cm, and the sample was developed using suitable solvents. For detection of spots, UV lamp irradiation with a wavelength of 254 nm, or heating on a hot plate after immersion of the plate into a 10% ethanol solution of 12 molybdo (VI) phosphoric acid n-hydrate, or an iodine adsorption method were used.

GC Analysis

Shimadzu GC-2014 was used, and as a column, a capillary column Agilent Technologies DB1-1MS (length 60 m, bore 0.25 mm, film thickness 0.25 μm) was used. Helium was used as a carrier gas, and a column linear velocity was adjusted to 30 cm/sec. The temperature of injection chamber was set to 150° C., and the temperature of detector (FID) was set to 280° C.

A sample was dissolved in ethyl acetate and prepared to be a 1 wt % solution, and then 0.5 μL of the solution obtained was injected into the injection chamber.

$^1$H NMR Analysis $^1$H NMR spectra were measured with a JEOL ECZ400S. Samples prepared in the examples or the like were dissolved in CDCl$_3$, and measurement was carried out with 4 times of accumulation at room temperature. In explaining nuclear magnetic resonance spectra obtained, s, d, t, q, quin, and m stand for singlet, doublet, triplet, quartet, quintet and multiplet, and br being broad, respectively. Moreover, tetramethylsilane (TMS) was used as an internal standard of the chemical shift δ=0 ppm.

Melting Point Measurement

Yanaco MP-S3 model Micro Melting Point Apparatus was used, and the indicated temperature was taken as melting point without correction.

Synthesis Example 1: Synthesis of γ-methyl-mevalonolactone methacrylate

γ-Methyl-mevalonolactonemethacrylate represented by formula (1a) was prepared according to the route shown in scheme [I-1]. The details are as follows.

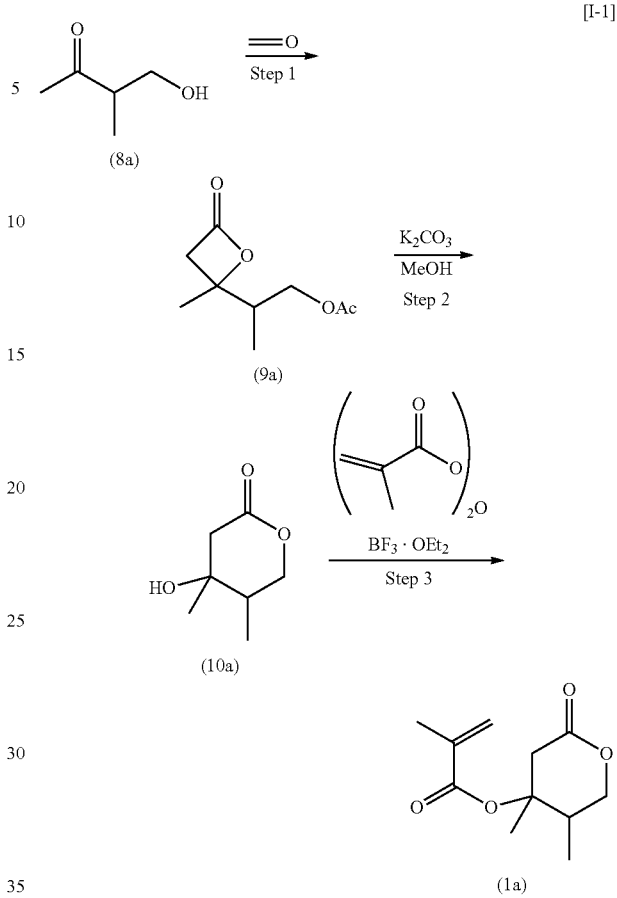

Step 1

To a solution of 4-hydroxy-3-methylbutan-2-one (8a) (10.2 g, 0.1 mol) in dichloromethane (50 mL) was added 0.38 mL (3 mmoL) of trifluoroboron ether complex at −50° C. under N$_2$, and ketene gas was introduced into the reaction mixture at a flow rate of 6.6 mmol/minute for 2 h with stirring. Meanwhile, temperature of the reaction mixture rose because of the exothermic reaction, and therefore dry ice was appropriately added to the cold bath to maintain the temperature of the reaction mixture between −42 and −44° C. After completion of the reaction, nitrogen gas was passed through the reaction mixture for 20 min to purge excessive ketene, and the temperature of the resulting mixture was raised to 0° C. and poured into saturated aqueous sodium hydrogen carbonate solution, and had been stirred overnight at room temperature. The resulting mixture was separated into two phases, and extraction from an aqueous layer was performed with dichloromethane 3 times, and then organic layers were combined and dried over anhydrous sodium sulfate.

The desiccant was filtered off, and the filtrate was concentrated under reduced pressure to obtain 37.6 g of crude product as an oily material. Diastereomer ratio was 25:75 by the analysis of $^1$H NMR.

The crude product was purified by silica gel column chromatography (n-heptane/ethyl acetate/triethylamine=60/30/10) to obtain 17.7 g of β-lactone (9a) as a diastereomer mixture. 95% yield, diastereomer ratio was 25:75.

In addition, both diastereomers (9a-x) and (9a-y) were able to be partly isolated, and were converted into (10a-x)

and (10a-y) in step 2, respectively, and their NOESY spectra of the compounds obtained were measured to determine relative configurations of (9a-x) and (9a-y) by tracing back therefrom. Both (9a-x) and (9a-y) were oily substances.

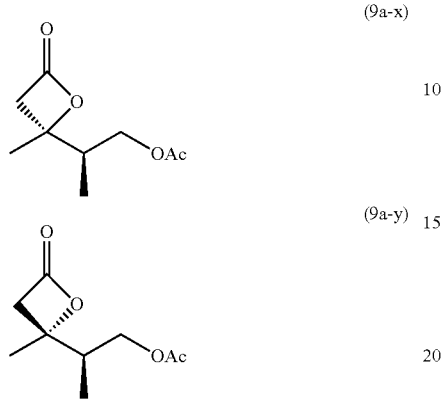

(9a-x)

(9a-y)

¹H-NMR (9a-x): 1.06 ppm (CH₃—CH), d, J=6.78 Hz; 1.50 ppm (CH₃ adjacent to β-lactone), s; 2.04 ppm (CH₃—COO), s; 2.27 ppm (CH), sex, J=6.78 Hz; 3.12 ppm (one H of CH₂ of β-lactone), d, J=16.27 Hz; 3.35 ppm (the other H of CH₂ of β-lactone), d, J=16.27 Hz; 4.02 ppm (CH₂—OAc), d, J=6.78 Hz.

¹H-NMR (9a-y): 1.06 ppm (CH₃—CH), d, J=7.00 Hz; 1.57 ppm (CH₃ adjacent to β-lactone), s; 2.07 ppm (CH₃—COO), s; 2.28 ppm (CH), qdd, J=7.00, 6.64, 5.19 Hz; 3.11 ppm (one H of CH₂ of β-lactone), d, J=16.25 Hz; 3.29 ppm (the other H of CH₂ of β-lactone), d, J=16.25 Hz; 4.09 ppm (one H of CH₂ adjacent to AcO), dd, J=11.26, 6.64 Hz; 4.20 ppm (the other H of CH₂ adjacent to AcO), dd, J=11.26, 5.19 Hz.

Step 2

To a mixture of 0.352 g (2.55 mmoL) of potassium carbonate and methanol (8.5 mL) was added dropwise 1.58 g (8.50 mmoL) of β-lactone (9a-x) in methanol (8.5 mL) was dissolved for 1 min under nitrogen. The resulting mixture was stirred at room temperature for 15 h, and then ice-cooled, and 10 mL of 1 M hydrochloric acid was added, and the resulting mixture was separated into two phases, and extraction from the aqueous layer was performed with 5 mL of ethyl acetate 4 times, and organic layers were combined and dried over anhydrous sodium sulfate. The desiccant was filtered off, and then the filtrate was concentrated under reduced pressure to obtain 1.20 g of crude product. The resulting crude product was purified by silica gel column chromatography (n-heptane/ethyl acetate=2/3) to afford 1.03 g of γ-methyl-mevalonolactone (10a-x) as an oily substance, 85% yield (GC purity 99.9%).

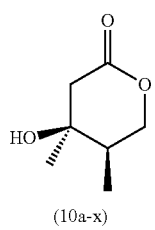

(10a-x)

¹H-NMR: 1.03 ppm (CH₃—CH), d, J=6.96 Hz; 1.26 ppm (CH₃—C—OH), s; 2.00 ppm (CH), m; 2.28 ppm (OH), br; 2.55 (one H of CH₂—CO), d, J=17.74 Hz; 2.66 ppm (the other H of CH₂—CO), d, J=17.74 Hz; 3.94 ppm (one H of CH₂—OCO), dd, J=11.44, 6.66 Hz; 4.57 ppm (the other H of CH₂—OCO), dd, J=11.44, 4.69 Hz.

NOESY: No cross peak was observed between ¹H at 1.26 ppm and ¹H at 3.94 ppm and between ¹H at 1.26 ppm and ¹H at 4.57 ppm.

According to the same method as described above, 0.454 g of γ-methyl-mevalonolactone (10a-y) was obtained from 0.700 g (3.76 mmol) of β-lactone (9a-y). Melting point was 70° C., 84% yield (GC purity 99.9%).

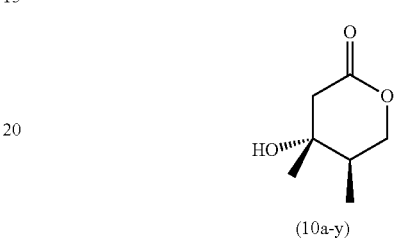

(10a-y)

¹H-NMR: 0.95 ppm (CH₃—CH), d, J=6.82 Hz; 1.31 ppm (CH₃—C—OH), s; 1.96 ppm (CH), m; 2.27 ppm (OH), br; 2.49 (one H of CH₂—CO), d, J=17.76 Hz; 2.70 ppm (the other H of CH₂—CO), d, J=17.76 Hz; 4.19 ppm (one H of CH₂—OCO), dd, J=11.28, 5.52 Hz; 4.26 ppm (the other H of CH₂—OCO), t, J=11.28 Hz.

NOESY: A cross peak was observed between ¹H at 1.31 ppm and ¹H at 4.26 ppm.

Step 3

To a solution of 0.144 g (1.00 mmoL) of γ-methyl-mevalonolactone (10a-y) and 0.231 g (1.50 mmoL) of methacrylic anhydride in toluene (2 mL) was added 0.14 mL (1.10 mmoL) of borontrifluoride-ether complex at room temperature under nitrogen, and the resulting mixture was heated to 40° C., and stirred at 40° C. for 3 h. After the reaction completed, the reaction mixture was cooled to room temperature, and 10 mL of toluene and 10 mL of water were added, and the mixture was further stirred for 10 min. It was separated into two phases, and extraction from the aqueous layer was performed with 5 mL of toluene 3 times, and organic layers were combined and dried over anhydrous magnesium sulfate. The desiccant was filtered off, and then the filtrate was concentrated under reduced pressure to obtain 284 mg of crude product. It was purified by silica gel column chromatography (n-heptane/ethyl acetate=2/1) to afford 161 mg of γ-methyl-mevalonolactone methacrylate (1a-y). 76% yield (GC purity 99.9%).

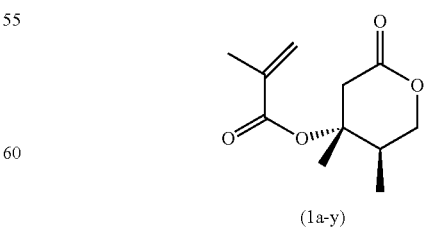

(1a-y)

¹H-NMR: 1.06 ppm (CH₃—CH), d, J=6.82 Hz; 1.63 ppm (CH₃—C—O), s; 1.91 ppm (CH₃—C—C), t, J=1.26 Hz; 2.07 ppm (CH), m; 2.57 (one H of CH₂—CO), d, J=18.52

Hz; 3.68 ppm (the other H of CH$_2$—CO), d, J=18.52 Hz; 4.27 ppm (CH$_2$—OCO), m; 5.56 ppm (H of terminal CH$_2$ in a Z configuration when viewed from CH$_3$ of a methacrylic group), quin, J=1.56 Hz; 6.14 ppm (H of terminal CH$_2$ in an E configuration when viewed from CH$_3$ of a methacrylic group), quin, J=1.18 Hz.

According to the same method as described above, 0.159 g of γ-methyl-mevalonolactone methacrylate (1a-x) was obtained from 0.144 g (1.00 mmol) of β-lactone (9a-x). The product was an oily substance, 75% yield (GC purity 99.9%).

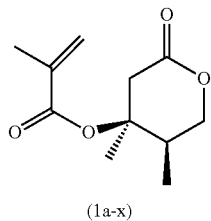

(1a-x)

$^1$H-NMR: 1.09 ppm (CH$_3$—CH), d, J=7.19 Hz; 1.56 ppm (CH$_3$—C—O), s; 1.89 ppm (CH$_3$—C=C), t, J=1.24 Hz; 2.69 ppm (CH), m; 2.91 (one H of CH$_2$—CO), d, J=17.85 Hz; 3.06 ppm (the other H of CH$_2$—CO), d, J=17.85 Hz; 4.00 ppm (one H of CH$_2$—OCO), dd, J=11.63, 6.94 Hz; 4.40 ppm (the other H of another of CH$_2$—OCO), dd, J=11.63, 4.56 Hz; 5.55 ppm (H of terminal CH$_2$ in a Z configuration when viewed from CH$_3$ of a methacrylic group), quin, J=1.54 Hz; 6.02 ppm (H of terminal CH$_2$ in an E configuration when viewed from CH$_3$ of a methacrylic group), dt, J=1.54, 0.77 Hz.

Synthesis Example 2: Synthesis of α-methyl-mevalonolactone Methacrylate

α-Methyl-mevalonolactone methacrylate represented by formula (1b) was prepared according to the route shown in scheme [II-1]. The details are as follows.

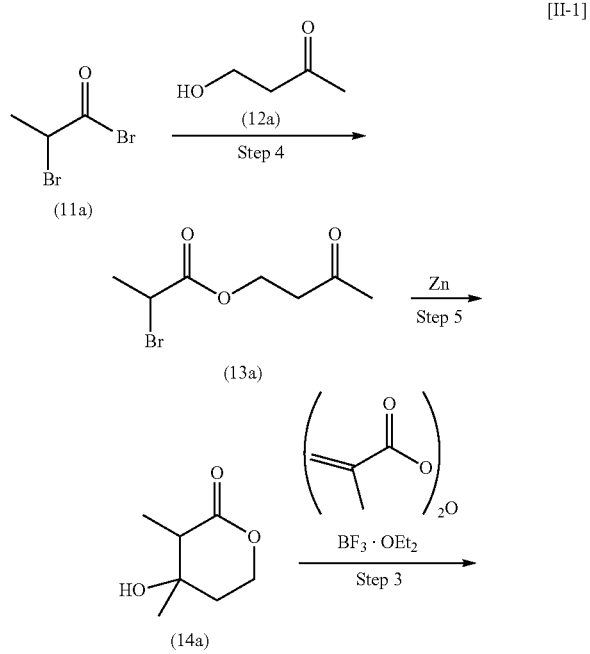

[II-1]

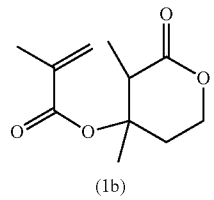

(1b)

Step 4

To an ice-cooled solution of 4-hydroxybutan-2-one (12a) (0.881 g, 10.0 mmoL) and triethylamine (1.02 g, 10.0 mmoL) in tetrafydrofuran (2.5 mL) was dropwise added a solution of α-bromopropionyl bromide (1.08 g, 5.00 mmoL) in tetrahydrofuran (2.5 mL) for 4 min under nitrogen. The resulting mixture was warmed to room temperature, and stirred at room temperature for 6 h, and then 10 mL of toluene and 10 mL of water were added to the reaction solution, and the resulting mixture was separated into two phases, and extraction from an aqueous layer was performed with 5 mL of toluene 3 times, and the organic layers were combined and dried over anhydrous magnesium sulfate. The desiccant was filtered off, and then the filtrate was concentrated under reduced pressure to obtain 1.10 g of crude product. The resulting product was purified by silica gel column chromatography (n-heptane/ethyl acetate=3/1) to afford 1.01 g of α-bromopropionic acid 3-oxobutyl ester (13a). A slightly yellow liquid, 90% yield (GC purity 99.0%).

$^1$H-NMR: 1.79 ppm (CH$_3$—CHBr), d, J=6.98 Hz; 2.20 ppm (CH$_3$—CO), s; 2.80 ppm (CH$_2$—CO), td, J=6.29, 2.34 Hz; 4.33 ppm (CHBr), q, J=6.98 Hz; 4.42 ppm (OCH$_2$), td, J=6.35, 1.32 Hz.

Step 5

To a mixture of 0.110 g (1.69 mmol) of zinc powder and tetrahydrofuran (1 mL) was added solution of 4.6 mg (0.05 mmol) of chlorotrimethylsilane in tetrahydrofuran (0.2 mL) at room temperature under nitrogen, and stirred for 5 min. And then to the reaction mixture was added 0.314 g (1.41 mmol) of a-bromopropionic acid 3-oxobutyl ester (13a) in tetrahydrofuran (6 mL) in 1 min at ambient temperature without cooling, while the reaction was exothermic. Stirring was continued for 2 h, and then the resulting mixture was ice-cooled, 10 mL of saturated aqueous ammonium chloride solution and 10 mL of toluene were added, the resulting mixture was separated into two phases, extraction from an aqueous layer was performed with 5 mL of ethyl acetate 3 times, and organic layers were combined and dried over anhydrous sodium sulfate. The desiccant was filtered off, and then the filtrate was concentrated under reduced pressure to obtain 0.205 g of crude product. The resulting product was purified by silica gel column chromatography (n-heptane/ethyl acetate=1/3) to afford 0.156 g of α-methyl-mevalonolactone (14a). 77% yield (GC purity as a diastereomer mixture 99.4%). The product was a diastereomer mixture having the isomer ratio of (14a-x):(14a-y)=86:14. Both of the isomers could be partially isolated, and therefore their structures were confirmed by $^1$H-NMR and a relative configuration was determined by a NOESY spectrum. The results indicated that (14a-x) and (14a-y) have relative configurations shown below, respectively.

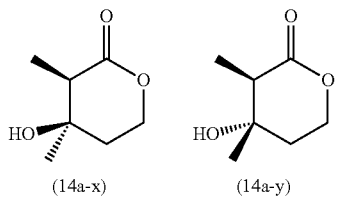

(14a-x)  (14a-y)

¹H-NMR (14a-x): 1.31 ppm (CH₃—CH), d, J=7.14 Hz; 1.38 ppm (CH₃—C—OH), s; 1.70 ppm (OH), br; 1.97 ppm (one H of CH₂CH₂—O), dt, J=9.43, 4.81 Hz; 2.06 ppm (the other H of CH₂CH₂—O), td, J=9.43, 4.81 Hz; 2.47 ppm (CH), q, J=7.14 Hz; 4.28 ppm (one H of CH₂—O), dt, J=11.43, 5.05 ppm; 4.54 ppm (the other H of CH₂—O), ddd, J=11.43, 9.34, 4.57 Hz.

NOESY: A cross peak was observed between ¹H at 2.06 ppm and ¹H at 2.47 ppm, whereas no cross peak was observed between ¹H at 1.38 ppm and ¹H at 4.27 ppm and between ¹H at 1.38 ppm and ¹H at 4.28 ppm.

¹H-NMR (14a-y): 1.22 ppm (CH₃—C—OH), s; 1.23 ppm (CH₃—CH), d, J=7.20 Hz; 1.93 ppm (one H of CH₂CH₂—O), dt, J=14.36, 4.92 Hz; 2.01 ppm (the other H of CH₂CH₂—O), ddd, 14.36, 9.15, 5.55 Hz; 2.50 ppm (OH), br; 2.64 ppm (CH), q, J=7.20 Hz; 4.26 ppm (one H of CH₂—O), ddd, J=11.49, 5.55, 4.86 ppm; 4.48 ppm (the other H of CH₂—O), ddd, J=11.49, 9.15, 4.86 Hz.

NOESY: A cross peak was observed between ¹H at 2.01 ppm and ¹H at 2.64 ppm and between ¹H at 1.22 ppm and ¹H at 4.26 ppm.

According to the same method as described in step 3, α-methyl-mevalonolactone methacrylate (1b) was prepared, and 0.151 g of α-methyl-mevalonolactone methacrylate (1b-x) was obtained from 0.144 g (1.00 mmol) of (14a-x). The product was a liquid at room temperature, 71% yield (GC purity 99.9%). Then, 0.157 g of α-methyl-mevalonolactone methacrylate (1b-y) was obtained from 0.144 g (1.00 mmol) of (14a-y). The product was a liquid at room temperature, 74% yield (GC purity 99.9%).

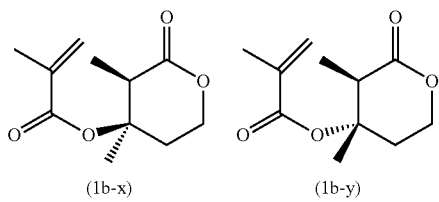

(1b-x)  (1b-y)

¹H-NMR (1b-x): 1.35 ppm (CH₃—CH), d, J=6.86 Hz; 1.66 ppm (CH₃—C—O), s; 1.88 ppm (CH₃—C=C), t, J=1.26 Hz; 2.12 ppm (one H of CH₂CH₂—O), ddd, 15.04, 8.29, 5.43 Hz; 2.84 ppm (the other H of CH₂CH₂—O), ddd, 15.04, 5.87, 4.75 Hz; 2.49 ppm (CH₃—CH), q, J=6.86 Hz; 4.20-4.31 ppm (CH₂—O), m; 5.55 ppm (one H of CH₂=C), quint, J=1.36 Hz; 6.03 ppm (the other H of CH₂=C), quin, J=1.36 Hz.

Synthesis Example 3: Synthesis of δ-methyl-mevalonolactone Methacrylate

Then, δ-methyl-mevalonolactone methacrylate represented by formula (1c) was prepared according to the route shown in scheme [I-3]. The detail are as follows.

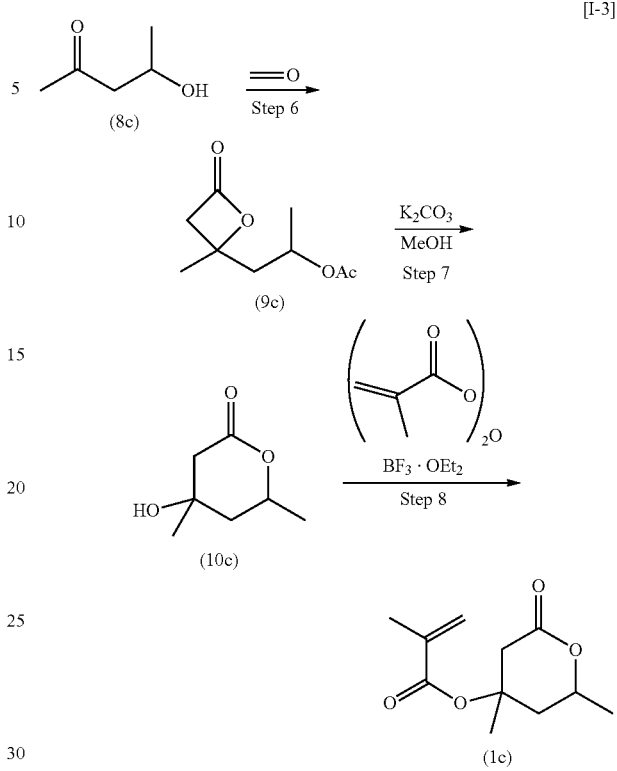

Step 6

Compound (8c) (60.5 g, 593 mmol) synthesized by a publicly-known method was dissolved in ethyl acetate (500 mL), and the resulting solution was cooled to 10° C. in an ice bath. To the mixture was added boron trifluoride-diethyl ether complex (2.4 mL, 19.0 mmol), and ketene gas was introduced into the resulting mixture. After completion of the reaction, the reaction mixture was washed with 20% aqueous sodium chloride solution, 5% aqueous sodium hydrogen carbonate solution (400 mL), and saturated aqueous sodium chloride solution (400 mL). The organic layer was concentrated under reduced pressure to obtain a crude compound (9c). The operation was carried out in 3 batches to afford 326.3 g of brown liquid.

Step 7

326.3 g of crude (9c) obtained in step 6 was dissolved in methanol (3710 mL), and the resulting solution was cooled to 10° C. To the solution was added potassium carbonate (170.2 g, 1231.3 mmol), and the resulting mixture was stirred for 4 h. Formic acid (169.4 g, 3679.9 mmol) and butyl acetate (1500 g) were added dropwise successively. Methanol was distilled off under reduced pressure, and a precipitated solid was filtered off by suction. The filtrate was concentrated and purified by silica gel column chromatography (effluent: ethyl acetate). The crude product obtained was recrystallized from toluene to afford compound (10c) as a white solid (92.5 g, 641.8 mmol). Overall yield in two steps was 36%.

Step 8

Compound (10c) (151.2 g, 1048.5 mmol), methacrylic anhydride (197.2 g, 1279.3 mmol) and Irganox 1076 (0.2 g, 0.3 mmol) were dissolved in toluene (700 mL). The resulting solution was heated to 40° C., and to the mixture was added dropwise boron trifluoride-diethyl ether complex (12.0 mL, 95.1 mmol) in 5 min, and then the resulting mixture was stirred for 5.5 h. After completion of the reaction, a reaction mixture was washed with 5% aqueous sodium hydrogen carbonate solution (1000 g) twice, and with a 10% aqueous sodium chloride solution (1000 g) once. The organic layer was concentrated under reduced pressure to obtain 223.8 g of crude compound (1-1). It was purified by WFE (wiped film evaporation) to afford a light yellow liquid (125.4 g, 590.8 mmol) as a mixture of isomers of compound (1c). 56% yield.

A small amount of (1c) obtained was purified by silica gel column chromatography to isolate (1c-x) and (1c-y), both of which structure were determined by $^1$H-NMR.

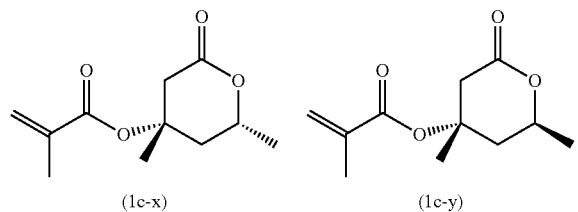

$^1$H-NMR (1c-x): 1.40 ppm (CH$_3$—CH), d, J=6.35 Hz; 1.66 ppm (β-position CH$_3$), s; 1.88 ppm (CH$_3$—C=C), t, J=1.15 Hz; 2.13 ppm (one H of CH$_2$CHCH$_3$—O), dd, J=14.58, 11.72 Hz; 2.37 ppm (the other H of CH$_2$CHCH$_3$—O), dd, J=14.58, 3.03 Hz; 2.71 ppm (one H of CH$_2$—CO), d, J=16.58 Hz, 2.91 ppm (the other H of CH$_2$—CO), d, J=16.58 Hz; 4.38 ppm (CH—O), dqd, J=11.72, 6.35, 3.03 Hz; 5.55 ppm (one H of CH$_2$=C), quint, J=1.15 Hz; 6.04 ppm (the other H of CH$_2$=C), quin, J=1.15 Hz.

$^1$H-NMR (1c-y): 1.38 ppm (CH$_3$—CH), d, J=6.35 Hz; 1.61 ppm (β-position CH$_3$), s; 1.88 ppm (CH$_3$—C=C), t, J=1.17 Hz; 1.60 ppm (one H of CH$_2$CHCH$_3$—O), dd, J=15.55, 11.75 Hz; 2.71 ppm (the other H of CH$_2$CHCH$_3$—O), dt, J=15.55, 2.23 Hz; 2.48 ppm (one H of CH$_2$—CO), t, J=1.17 Hz, 3.18 ppm (the other H of CH$_2$—CO), dd, J=17.43, 2.23 Hz; 4.58 ppm (CH—O), dqd, J=11.75, 6.35, 2.63 Hz; 5.56 ppm (one H of CH$_2$=C), quint, J=1.17 Hz; 6.02 ppm (the other H of CH$_2$=C), quin, J=1.15 Hz.

Test Example

According to Test Examples described below, water solubility of a polymerizable compound (Example) described herein and hydroxylactone (Comparative Example) as a precursor thereof were examined.

Example 1

In 10 mL of water, 0.500 g of the compound represented by formula (14a-x) was dissolved at room temperature, and 10 mL of ethyl acetate was added thereto, and the resulting mixture was stirred for 10 min, and then the organic layer was dried over anhydrous sodium sulfate. The desiccant was filtered off, and then the filtrate was concentrated under reduced pressure. The weight of the residue was 0.101 g.

Comparative Example 1

In 10 mL of water, 0.500 g of a compound represented by formula (15), namely, mevalonolactone was dissolved at room temperature, and 10 mL of ethyl acetate was added thereto, and the resulting mixture was stirred for 10 min, and then the organic layer was dried over anhydrous sodium sulfate. The desiccant was filtered off, and then the filtrate was concentrated under reduced pressure. Then weight of the residue was 0.080 g.

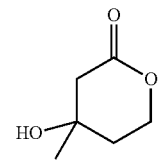

The compound used in Example 1 obviously has lower water solubility, as compared with the compound used in Comparative Example 1. Accordingly, the polymerizable compound of the invention can be produced more easily than mevalonolactone methacrylate.

What is claimed is:

1. A compound, represented by formula (1-3):

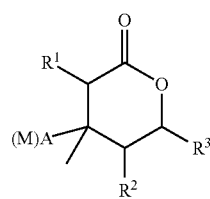

wherein, in formula (1-3), (M)A is a (meth)acryloyloxy group, one of $R^1$ and $R^2$ is a saturated hydrocarbon group having 1 to 4 carbons, and the other one is a hydrogen atom, and $R^3$ is a hydrogen atom.

2. A compound, represented by formula (1-4):

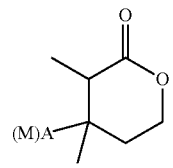

wherein, in formula (1-4), (M)A is a (meth)acryloyloxy group.

3. A compound, represented by formula (1-5):

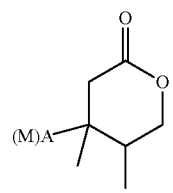

wherein, in formula (1-5), (M)A is a (meth)acryloyloxy group.

4. A polymerizable composition, containing at least one compound according to claim 1.

5. A polymerizable composition, containing at least one compound according to claim 2.

6. A polymerizable composition, containing at least one compound according to claim 3.

* * * * *